(12) United States Patent
Voigt (10) Patent No.: US 11,896,520 B2
(45) Date of Patent: Feb. 13, 2024

(54) TEMPERATURE TREATMENT APPARATUS (71) Applicant: BANDICOOL PTY LTD, Middle Park (AU)

(72) Inventor: Belinda Voigt, Middle Park (AU)

( * ) Notice: Subject to any disclaimer, the term of this patent is extended or adjusted under 35 U.S.C. 154(b) by 436 days.

(21) Appl. No.: 16/767,426

(22) PCT Filed: Nov. 27, 2018

(86) PCT No.: PCT/AU2018/000234
§ 371 (c)(1),
(2) Date: May 27, 2020

(87) PCT Pub. No.: WO2019/100103
PCT Pub. Date: May 31, 2019

(65) Prior Publication Data
US 2021/0361475 A1    Nov. 25, 2021

(30) Foreign Application Priority Data
Nov. 27, 2017  (AU) ................... 2017904786

(51) Int. Cl.
*A61F 7/02* (2006.01)
*A61F 7/10* (2006.01)

(52) U.S. Cl.
CPC .............. *A61F 7/02* (2013.01); *A61F 7/10* (2013.01); *A61F 2007/023* (2013.01);
(Continued)

(58) Field of Classification Search
CPC .............. A61F 5/01; A61F 2007/023; A61F 2013/00187; A61F 5/0106; A61F 2007/0001; A61F 2007/0086; A61F 7/10; A61F 13/0203; A61F 2007/0295; A61F 2013/002; A61F 13/0213; A61F 2007/0056; A61F 7/00; A61F 7/106; A61F 2007/0098; A61F 2013/0017; A61F 2013/00519; A61F 7/03; A61F 2007/0063; A61F 2007/0095;
(Continued)

(56) References Cited

U.S. PATENT DOCUMENTS 4,055,188 A    10/1977  Pelton
5,148,804 A *   9/1992  Hill ..................... A61F 7/10
                                                607/108
(Continued)

FOREIGN PATENT DOCUMENTS

WO    WO 90/01911 A1    3/1990

*Primary Examiner* — Ophelia A Hawthorne
(74) *Attorney, Agent, or Firm* — Edwin D. Schindler (57) ABSTRACT

A temperature treatment apparatus includes a body made from a flexible and expandable material for attachment to a predetermined region of the human body requiring treatment with the body having a space formed therein, and a temperature radiating element shaped to be received within the space of the body and being configured to have a soft and malleable shape profile to apply temperature treatment to the predetermined region of the human body. The temperature radiating element includes an inner pouch containing a first phase change material that is able to be inserted within an outer pouch having a second phase change material, so that, upon insertion, the inner pouch is substantially encapsulated within the second phase change material of the outer pouch.

9 Claims, 11 Drawing Sheets

(52) U.S. Cl.
CPC ......... *A61F 2007/0219* (2013.01); *A61F 2007/0231* (2013.01); *A61F 2007/0268* (2013.01); *A61F 2007/0292* (2013.01); *A61F 2007/108* (2013.01)

(58) Field of Classification Search
CPC ...... A61F 2007/0219; A61F 2007/0238; A61F 2007/101; A61F 5/34; A61F 7/02; A61F 2007/0207; A61F 2007/0223; A61F 2007/0279; A61F 2007/0266; A61F 2007/0088; A61F 5/0111; A61H 7/001
USPC ........................................................ 607/108
See application file for complete search history.

(56) References Cited

U.S. PATENT DOCUMENTS

| | | | |
|---|---|---|---|
| 5,843,145 A | 12/1998 | Brink | |
| 2007/0130840 A1 | 6/2007 | Jouhannet | |
| 2008/0275534 A1 | 11/2008 | Noel | |
| 2015/0272775 A1* | 10/2015 | Chehab | A61F 7/10 607/114 |

* cited by examiner

TEMPERATURE TREATMENT APPARATUS

RELATED APPLICATIONS

The present invention claims priority from Australian provisional patent application No. 2017904786, filed 27 Nov. 2017, the entire contents of which are incorporated herein by reference

FIELD OF INVENTION

The present invention relates generally to an apparatus for applying temperature treatment to an injury on a person's body, and in particular, to an apparatus for attachment to a limb or region of a person's body that is able to more appropriately target an injury site to apply heat or cold compression to that injury site.

BACKGROUND OF THE INVENTION

Cold and heat therapy are well known means by which to treat a variety of injuries, such as strained muscles and ligaments, as well as joint sprains and strains. The application of ice to an injured site is a well-established practice for treating such an injury as it functions to slow down blood flow to the injury site, thus reducing swelling and pain at the site and promoting healing.

In sporting applications where muscle injury and joint sprains and strains are common, a variety of different types of packs have been proposed to apply such ice treatment to an injured site. As ice is typically hard and defined in shape, it is difficult for ice cubes or blocks to readily adapt to the shape of a user's limb or body for application. Whilst smaller cubes or pieces of ice can be used, it is typically either tied around a user's limb or held in place by the user for applying the treatment, often resulting in the ice pack shifting or becoming displaced and failing to correctly treat the injured site, especially if the user is mobile. To address the difficulty in handling ice packs, packs employing cooling gels and various other such substances have been proposed. Such gels are able to be quickly chilled or frozen to a desired treatment temperature and are able to flow in such a state so as to better conform to a shape of the user's body requiring treatment. However, such gels are also prone to heat up quickly when applied to a user's body and are often retained in in packs made from heavy duty materials that do not readily facilitate efficient heat transfer from the gel or frozen material to the injured site.

For this reason, in most situations the application of ice to the injured site has retained its popularity and in order to retain the ice in position cling wrap and other materials have been employed to wrap the ice in position about the limb or region of the body such that the ice is captured in position. Whilst this may work in practice, it is difficult to do by one-self and is wasteful of materials, such as the wrapping material, which is often disregarded after use.

Thus, there is a need to provide a treatment system that is capable of being applied to various regions of a person's body in a secure manner and which are configured to apply the temperature treatment directly and efficiently to the injured site in a simple and effective manner.

The above references to and descriptions of prior proposals or products are not intended to be, and are not to be construed as, statements or admissions of common general knowledge in the art. In particular, the following prior art discussion does not relate to what is commonly or well known by the person skilled in the art, but assists in the understanding of the inventive step of the present invention of which the identification of pertinent prior art proposals is but one part.

STATEMENT OF INVENTION

According to a first aspect, there is provided a temperature treatment apparatus comprising:
  a body made from a flexible and expandable material for attachment to a predetermined region of the human body requiring treatment, the body having a space formed therein; and
  a temperature radiating element shaped to be received within the space of the body and being configured to have a soft and malleable shape profile to apply temperature treatment to the predetermined region of the human body;
  wherein the temperature radiating element comprises an inner pouch containing a first phase change material that is insertable within an outer pouch comprising a second phase change material, such that, upon insertion, the inner pouch is substantially encapsulated within the second phase change material of the outer pouch.

The inner pouch and the outer pouch of the temperature radiating element may be freezable for applying cold therapy to the predetermined region of the human body.

The body may be configured to be mounted to the predetermined region of the human body such that the temperature radiating element is located over the predetermined region of the human body requiring treatment so as to apply thermal treatment thereto whilst the body also provides compression treatment to the same predetermined region.

The body may comprise one or more arm members configured to extend around said human body, said arm members being secured with respect to said human body such that the body applies a compression force to the predetermined region of the human body.

The inner pouch may be configured to comprise a plurality of individual pockets containing said first phase change material. The plurality of individual pockets may be movable relative to each adjacent pocket. When the inner pouch is insertable within the outer pouch comprising a second phase change material, the second phase change material being configured to flow over and between the plurality of individual pockets so as to substantially encapsulate the individual pockets within the second phase change.

In one form, the first phase change material may have a freezing point that is substantially the same as the second phase change material. In another form, the first phase change material may have a freezing point that is higher than the freezing point of the second phase change material. The second phase material may be a soft material when frozen and may form a soft layer about the first phase material.

According to a second aspect, there is provided a temperature radiating element comprising:
  an inner pouch having a first phase change material contained therein; and
  an outer pouch comprising a second phase change material;
  wherein, the inner pouch is housed within the outer pouch such that the inner pouch is substantially encapsulated within the second phase change material of the outer pouch.

The inner pouch may comprise a plurality of individual pockets, each individual pocket may be substantially filled with the first phase change material.

The plurality of individual pockets may be separated from each other to provide a degree of movement of one pocket with respect to an adjacent pocket.

When the inner pouch is located within the outer pouch, the second phase change material may be free to flow between and over the individual pockets of the first pouch to substantially encapsulate the pockets within the second phase change material.

In a first form, the first phase change material and the second phase change material may have substantially the same freezing point. In another form, the second phase change material has a more depressed freezing point than the first phase change material.

BRIEF DESCRIPTION OF THE DRAWINGS

The invention may be better understood from the following non-limiting description of preferred embodiments, in which:

FIG. 7 is a top view of a temperature treatment apparatus in accordance with a fourth embodiment of the present invention;

DETAILED DESCRIPTION OF THE DRAWINGS

Preferred features of the present invention will now be described with particular reference to the accompanying drawings. However, it is to be understood that the features illustrated in and described with reference to the drawings are not to be construed as limiting on the scope of the invention.

The present invention will be described below in relation to the application of cold or ice treatment to an injury on a person's body. Such an application is configured to locate a cold source proximal the injury to facilitate cold therapy in association with compression therapy to the injury. However, it will be appreciated by those skilled in the art that the present invention could equally be employed to apply heat therapy to a site on an individual's body by simply changing the internal energy source from a cold source to a heating source, as will be appreciated by those skilled in the art.

Figure 1:
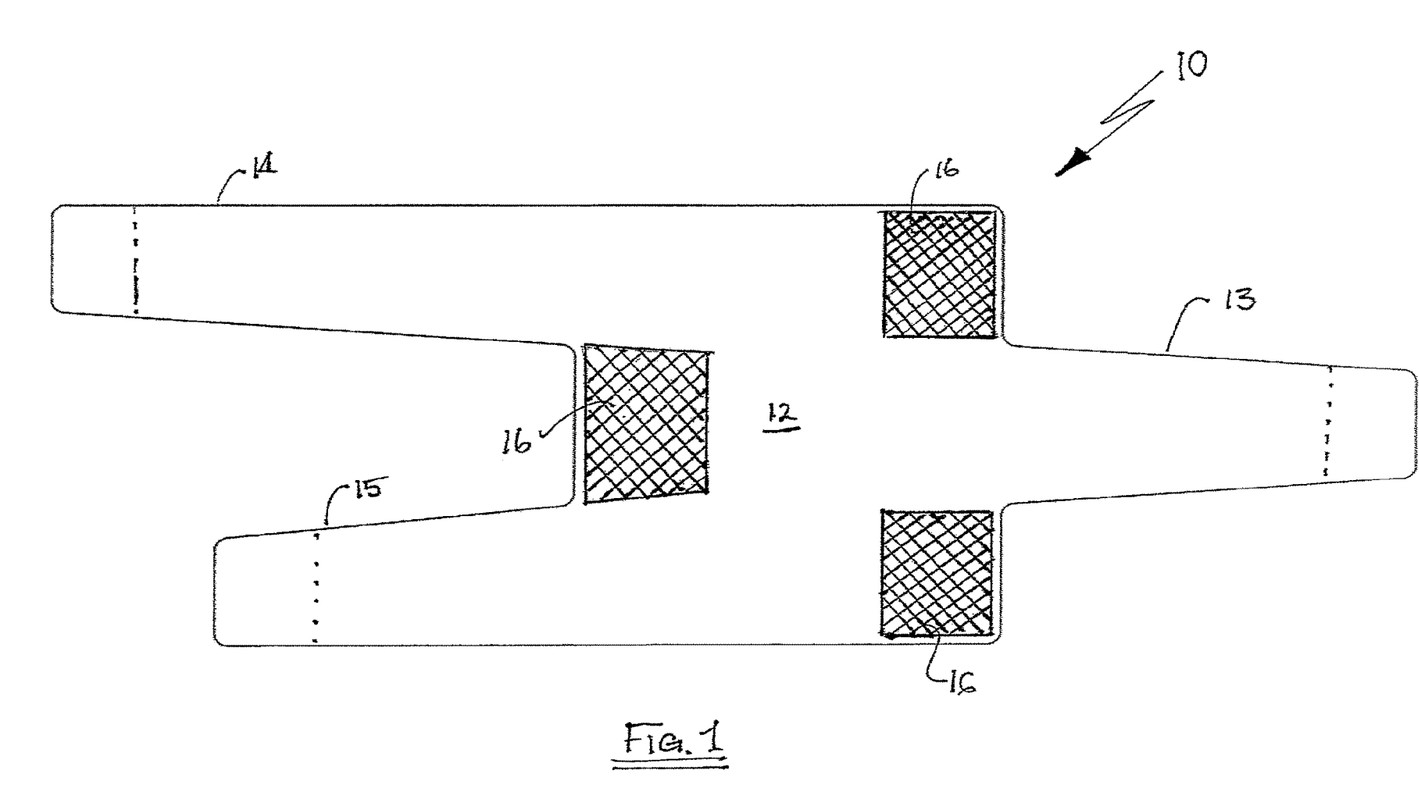
FIG. 1 is a top view of a temperature treatment apparatus in accordance with a first embodiment of the present invention.
Figure 2:
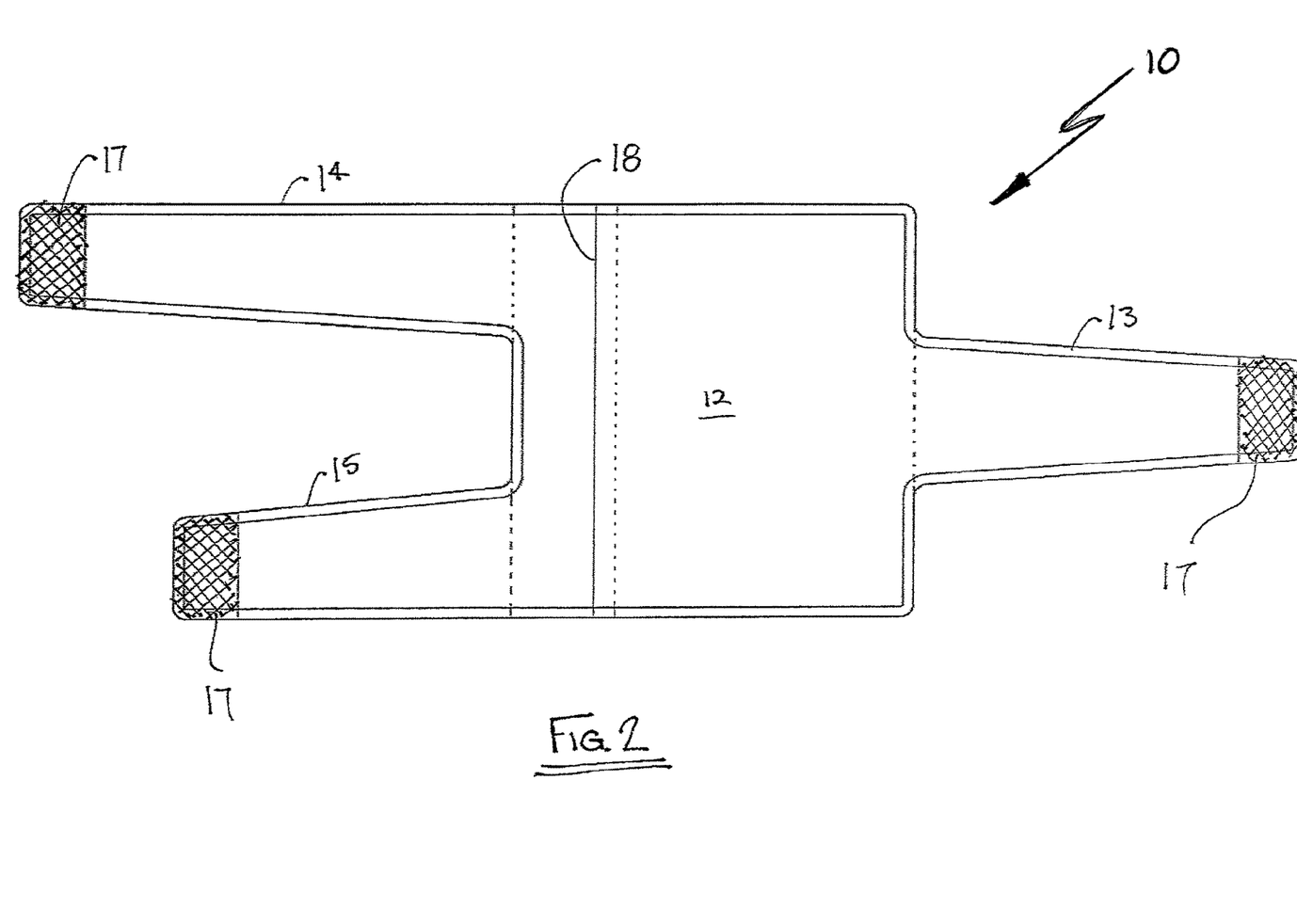
FIG. 2 is a bottom view of the temperature treatment apparatus of FIG. 1.

Referring to FIGS. 1 and 2, there is depicted a cold therapy treatment apparatus 10 in accordance with one embodiment of the present invention. The apparatus 10 is made from a synthetic rubber material that is flexible and expandable so as to apply compression about the injury site in association with locating the cold source adjacent the injury site. The synthetic rubber material may be neoprene or any other material having sufficient elasticity and expandability.

The apparatus 10 comprises a central body portion 12 that is configured to function as a pouch into which a cold source is to be positioned for application of cold therapy to an injury site. The central body portion 12 represents a large, substantially rectangular region, having an interior surface area, as is shown in FIG. 2, which is to be positioned over the injury. A slot or opening 18 is provided in the central body portion 12 to facilitate insertion of a cold pack (not shown) into the pouch. The structure of the cold pack will be described in more detail below, but is essentially configured to cover the surface area of the central body portion to maximise application of cold therapy to the injury.

To retain the apparatus 10 in position on the limb of the individual, namely about the knee of an individual suffering with a knee injury, three locating arm members 13, 14, and 15 are provided. As is best shown in FIG. 2, an inner surface of the distal end of each of the arm members 13, 14 and 15 is provided with a fastener portion 17, such as a patch of hook members forming one part of a hook and loop fastener, such as Velcro®. The fastener portion 17 is configured to attach to a corresponding mounting portion 16 provided on an external surface of the central body portion 12, which is typically a patch of loop members forming the other part of the hook and loop fastener. The arm members are configured to pass around the leg of the individual, adjacent the individual's knee so as to securely retain the apparatus 10 in position and to apply a compression therapy to the injury as well. In the embodiment as shown the arm member 14 is configured to extend around the lower thigh of the individual, the arm member 13 about the knee of the individual, and the arm member 15 about the upper part of the individual's lower leg. As a result, each of the arm members 13, 14, 15 have a different length.

It will be appreciated that when the apparatus 10 is fixed about the knee of the individual it can be rotated so as to apply cold therapy to the desired region of the user's knee, depending upon the type of injury being treated. When positioned and secured in this manner the apparatus 10 is able to target the injury, applying both cold therapy and compression therapy.

Figure 3:
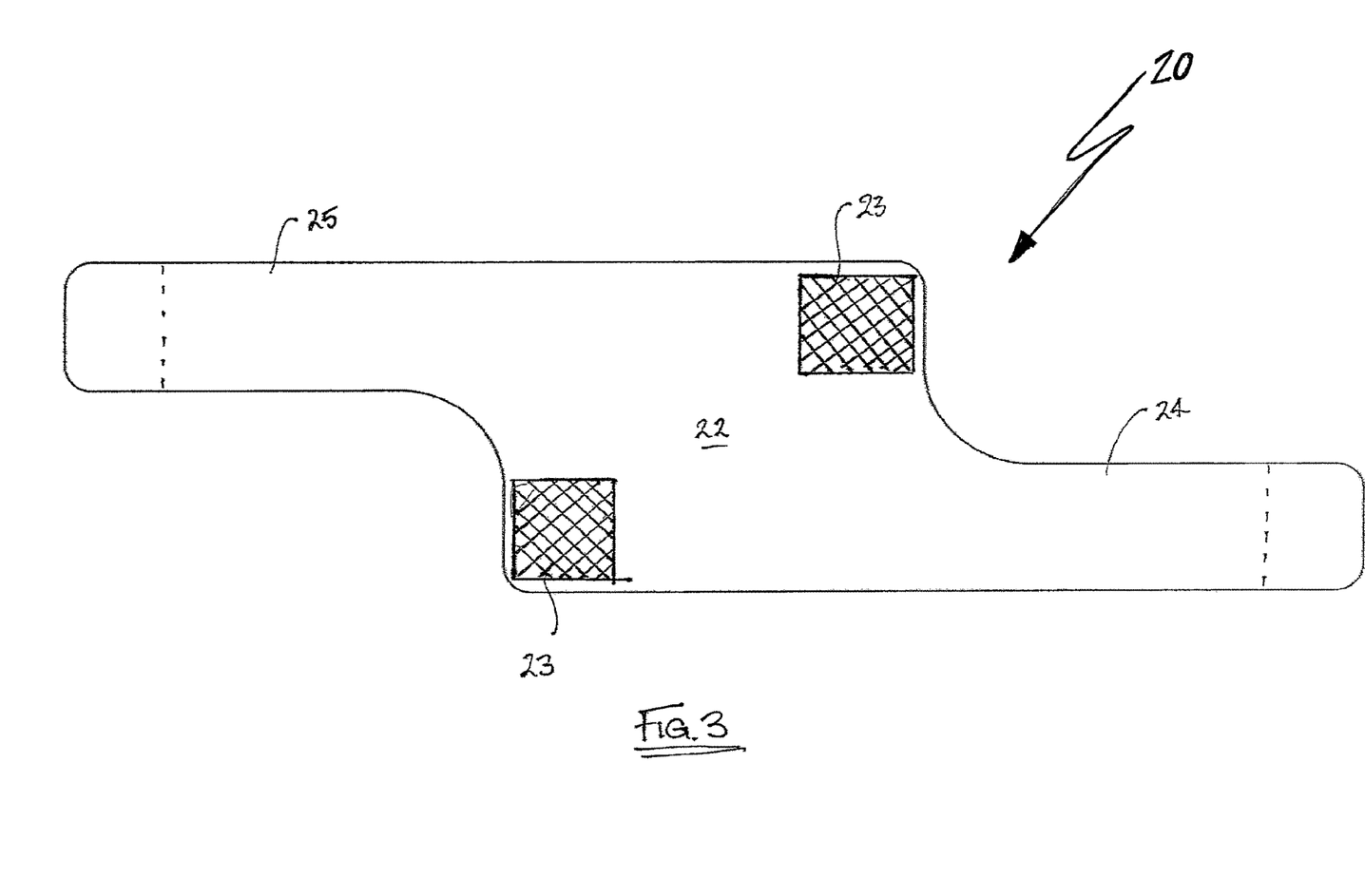
FIG. 3 is a top view of a temperature treatment apparatus in accordance with a second embodiment of the present invention.
Figure 4:
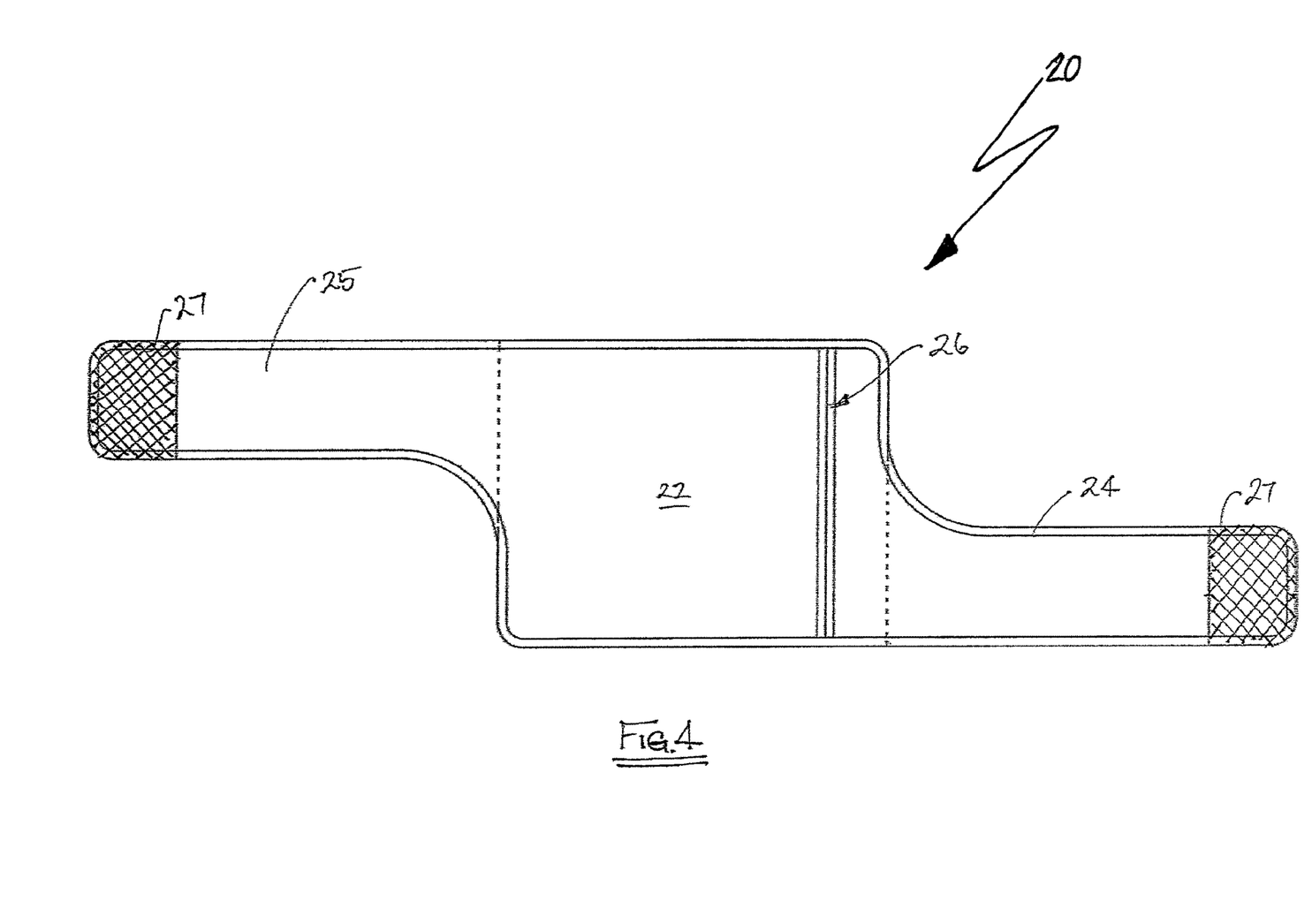
FIG. 4 is a bottom view of the temperature treatment apparatus of FIG. 3.

An alternative embodiment of a cold therapy treatment apparatus in accordance with the present invention is depicted in FIGS. 3 and 4 as reference numeral 20. In this embodiment, the apparatus 20 is intended for use on any limb where an injury may occur and is also made from a flexible and expandable synthetic rubber material such as neoprene.

The apparatus 20 comprises a central body portion 22 that is configured to function as a pouch into which a cold source is to be positioned for application of cold therapy to an injury site. The central body portion 22 represents a large, substantially rectangular region, having an interior surface area, as is shown in FIG. 4, which is to be positioned over the injury. An opening 26 is provided in the central body portion 22 to facilitate insertion of a cold pack (not shown) into the pouch formed by the central body portion. The structure of the cold pack will be described in more detail below, but is essentially configured to cover the surface area of the central body portion to maximise application of cold therapy to the injury. The opening 26 is provided with a closure, such as a zipper to seal the pouch such that the cold pack is retained within the central body portion 22. The pouch or pocket is lined or otherwise finished to be water resistant such that the user wearing the apparatus stays dry and not be in direct contact with the cold source.

To retain the apparatus 20 in position on a limb of the individual, namely about an arm, wrist, elbow, neck, foot and the like, a pair of locating arm members 24, 25 are provided. As is best shown in FIG. 4, an inner surface of the distal end of each of the arm members 24 and 25 is provided with a fastener portion 27, such as a patch of hook members forming one part of a hook and loop fastener, such as Velcro®. The fastener portion 27 is configured to attach to a corresponding mounting portion 23 provided on an external surface of the central body portion 22, which is typically a patch of loop members forming the other part of the hook and loop fastener. The arm members 24, 25 are configured to pass around the arm or leg of the individual, adjacent the injured area, so as to securely retain the apparatus 20 in position and to apply compression therapy to the injury region as well. In the embodiment as shown, each arm member 24, 25 is substantially the same length and may be wound around the individual's limb as to secure the apparatus in position.

It will be appreciated that when the apparatus 20 is fixed about the limb of the individual it can be rotated so as to apply cold therapy to the desired region, depending upon the type of injury being treated. When positioned and secured in this manner the apparatus 10 is able to target the injury, applying both cold therapy and compression therapy thereto.

Figure 5:
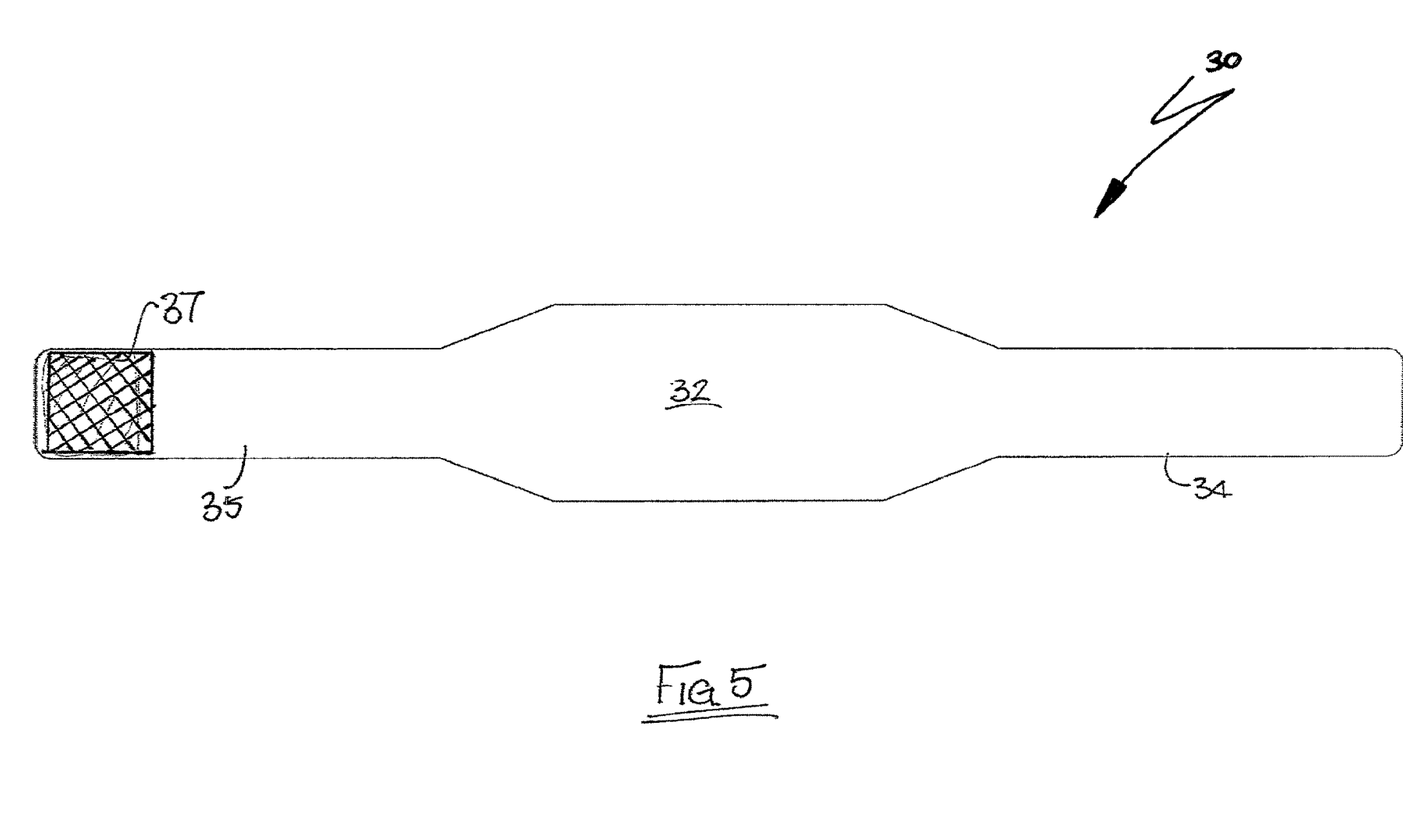
FIG. 5 is a top view of a temperature treatment apparatus in accordance with a third embodiment of the present invention.
Figure 6:
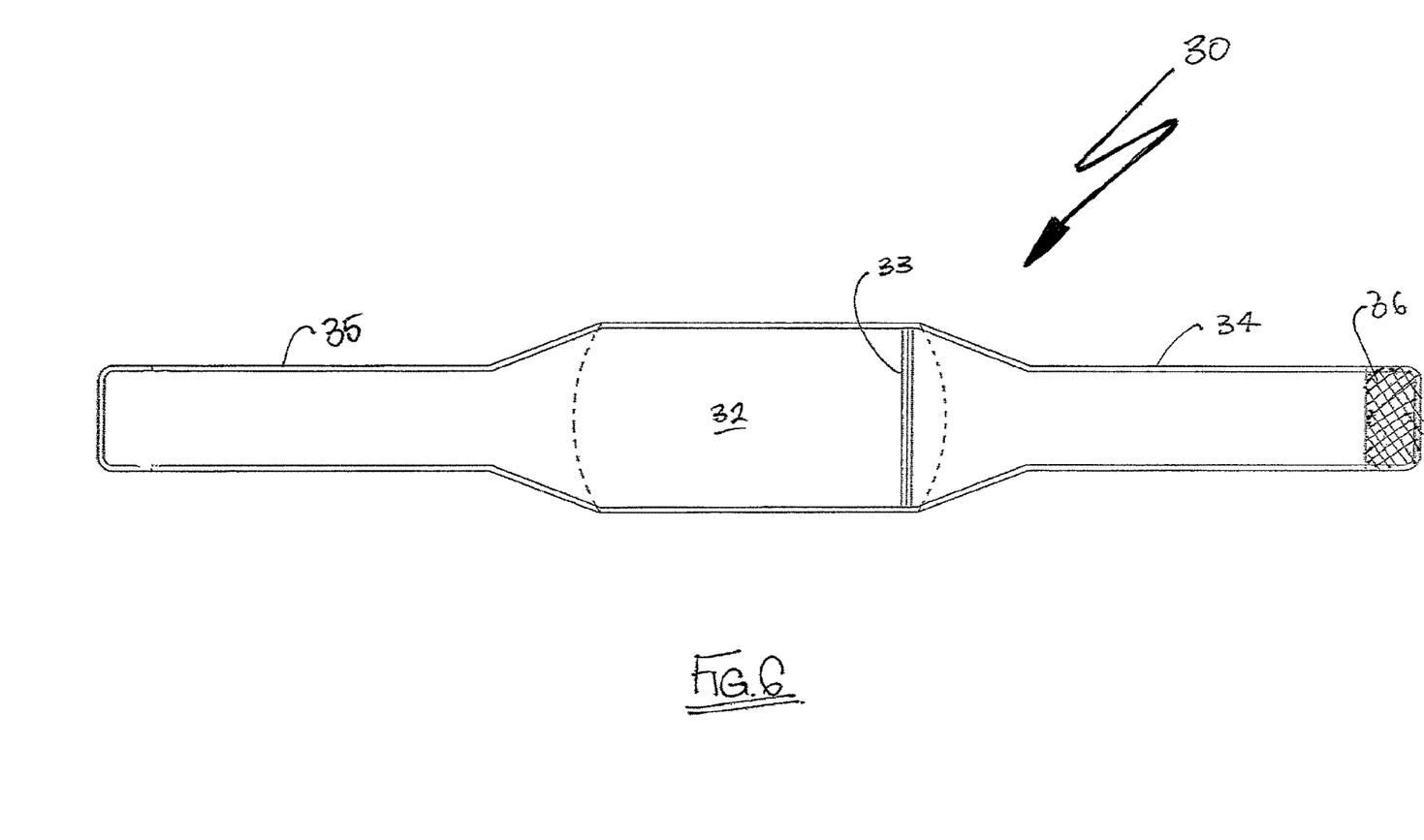
FIG. 6 is a bottom view of the temperature treatment apparatus of FIG. 5.

Yet another embodiment of a cold therapy treatment apparatus in accordance with the present invention is depicted in FIGS. 5 and 6 as reference numeral 30. In this embodiment, the apparatus 30 is intended for use on the back or torso of an individual where an injury may occur and is also made from a flexible and expandable synthetic rubber material such as neoprene.

The apparatus 30 comprises an elongate central body portion 32 that is configured to function as a pouch into which a cold source is to be positioned for application of cold therapy to an injury site. The central body portion 32 represents a long, substantially rectangular pouch region, having an interior surface area, as is shown in FIG. 6, which is to be positioned over the injury. An opening 33 is provided in the central body portion 32 to facilitate insertion of a cold pack (not shown) into the elongate pouch formed within the central body portion 32. The structure of the cold pack will be described in more detail below, but is essentially configured to cover the surface area of the central body portion 32 to maximise application of cold therapy to the injury site. The opening 26 is provided with a closure, such as a zipper to seal the pouch such that the cold pack is retained within the central body portion 32.

To retain the apparatus 30 in position on a limb of the individual, namely about the individuals back or torso, a pair of elongate locating arm members 34, 35 are provided. As is best shown in FIG. 6, an inner surface of the distal end of arm member 34 is provided with a fastener portion 27, such as a patch of hook members forming one part of a hook and loop fastener, such as Velcro®. The fastener portion 27 is configured to attach to a corresponding mounting portion 23 provided on an external surface of the distal end of the other arm member 35, which is typically a patch of loop members forming the other part of the hook and loop fastener. The arm members 34 and 35 are configured to extend around the torso of the individual such that the central body portion 32 is able to be located adjacent the injured area or area to be treated, so as to apply both cold therapy and compression therapy to the injury region.

It will be appreciated that when the apparatus 30 is fixed about the torso of the individual it can be rotated so as to apply cold therapy to the desired region, depending upon the type of injury being treated. When positioned and secured in this manner the apparatus 10 is able to target the injury, applying both cold therapy and compression therapy thereto.

Figures 8A, 8B:
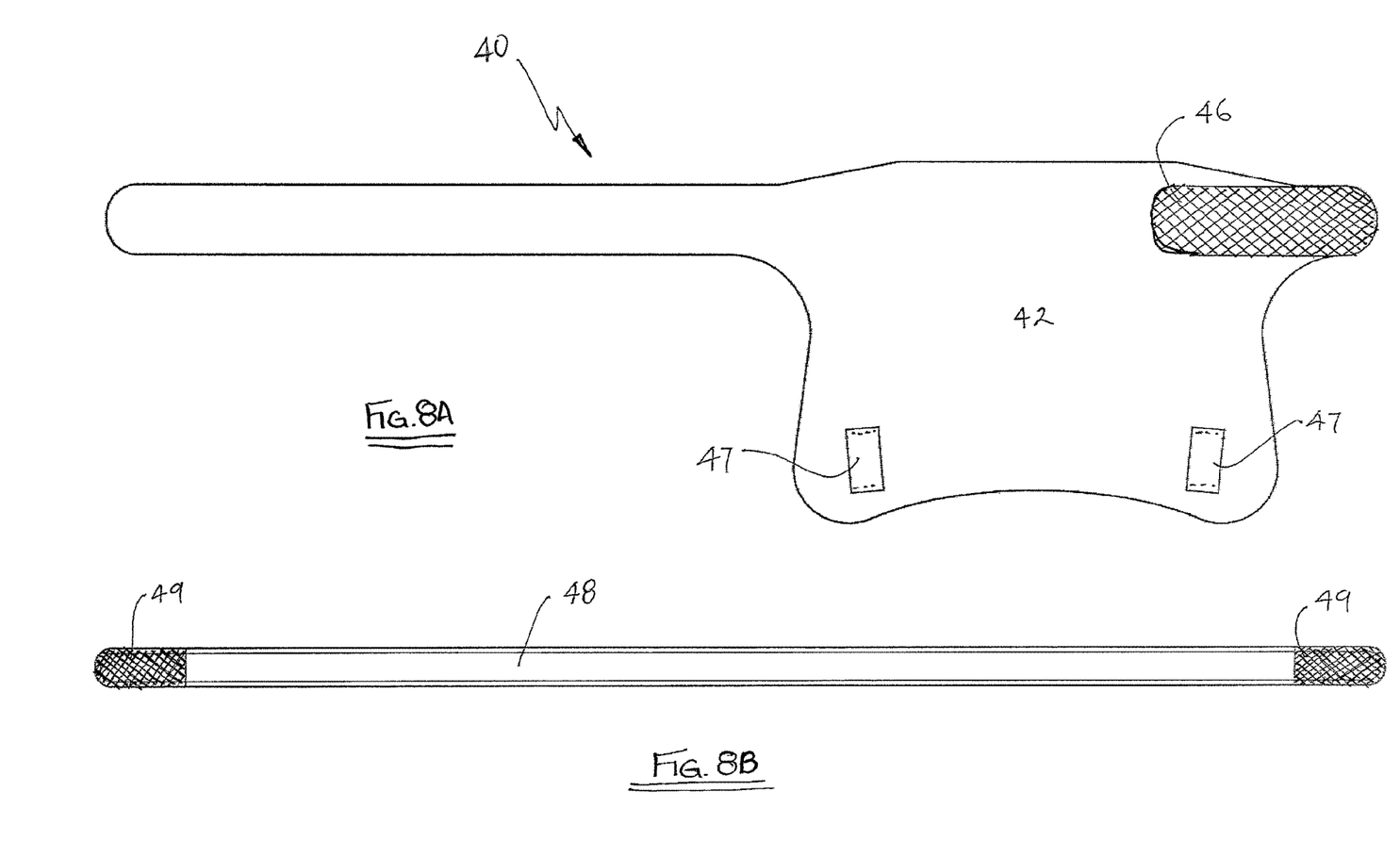
FIG. 8A is a bottom view of the temperature treatment apparatus of FIG. 7.
FIG. 8B is a plan view of a strap for use with the temperature treatment apparatus of FIGS. 7 and 8.

Yet another embodiment of a cold therapy treatment apparatus in accordance with the present invention is depicted in FIGS. 7 and 8 as reference numeral 40. In this embodiment, the apparatus 40 is intended for use on the hip or shoulder of an individual where an injury may occur and is also made from a flexible and expandable synthetic rubber material such as neoprene.

The apparatus 40 comprises a central body portion 42 that is configured to function as a pouch into which a cold source is to be positioned for application of cold therapy to the injury site. The central body portion 42 represents a substantially rectangular pouch region, having an interior surface area, as is shown in FIG. 7, which is to be positioned over the injury site. An opening 43 is provided in the central body portion 42 to facilitate insertion of a cold pack (not shown) into the pouch formed within the central body portion 42. The structure of the cold pack will be described in more detail below, but is essentially configured to substantially cover the surface area of the central body portion 42 to maximise application of cold therapy to the injury site. The opening 43 is provided with a closure, such as a zipper to seal the pouch such that the cold pack is retained within the central body portion 42.

To retain the apparatus 40 in position about the individual's hip or shoulder of the individual, the apparatus 40 is positioned on the body such that the interior surface of the central body portion 42 is located over the injury site. The apparatus 40 has one long securing arm member 44 which is of sufficient length to extend about the waist of the individual, or around the upper torso or arm of the individual. As is best shown in FIG. 7, an inner surface of the distal end of arm member 44 is provided with a fastener portion 45, such as a patch of hook members forming one part of a hook and loop fastener, such as Velcro®. The fastener portion 45 is configured to attach to a corresponding mounting portion 46 provided on an external surface of the central body portion 42, which is typically a patch of loop members forming the other part of the hook and loop fastener, which is located on the opposing side of the central body portion 42, as is best shown in FIG. 8A.

The outer surface of the central body portion is also provided with a pair of loops 47 to enable a separate strap 48 (FIG. 8B) to be used to further stabilise and secure the apparatus 40 in position. To use the separate strap 48, once the apparatus is located over the injury site in the manner as discussed above. The separate strap 48 is threaded through the loops 47 and secured at either end by way of the complimentary hook and loop fasteners 49. This additional means for securing the apparatus 40 provides additional support to better apply both cold therapy and compression therapy to the injury region.

Figure 9:
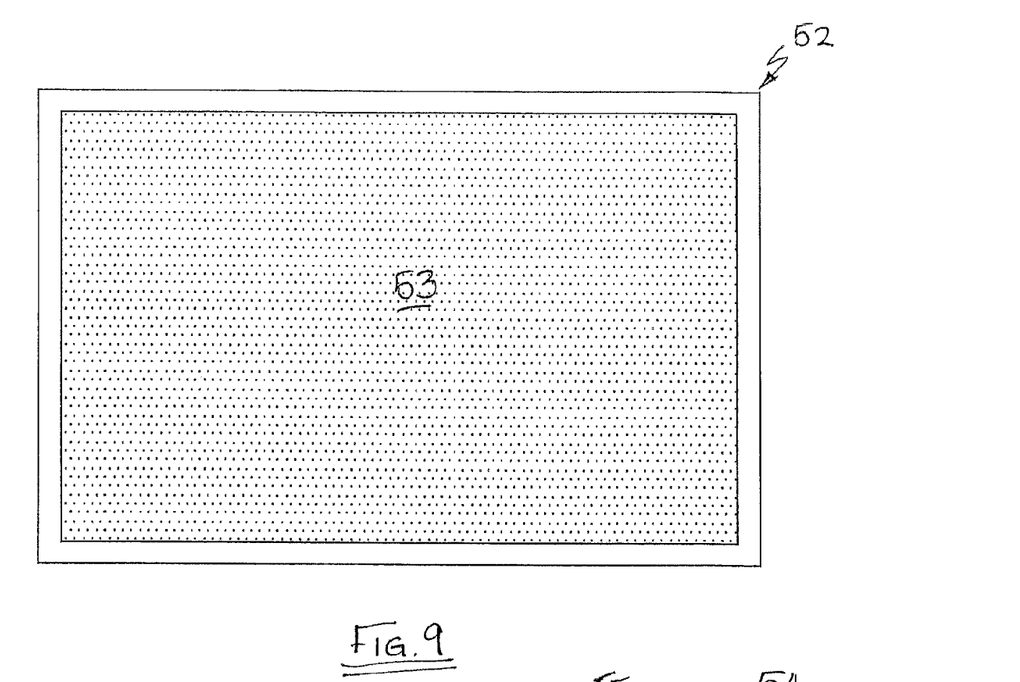
FIG. 9 is a plan view of an outer pouch of a cold pack in accordance with an embodiment of the present invention.
Figure 10:
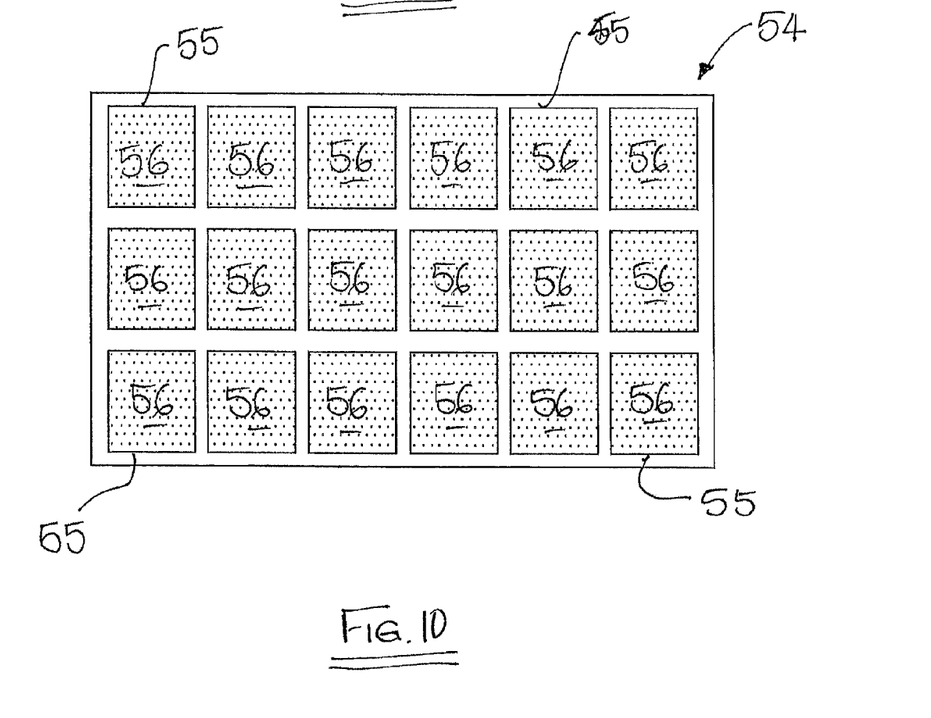
FIG. 10 is a plan view of an inner pouch of a cold pack in accordance with an embodiment of the present invention.
Figure 11:
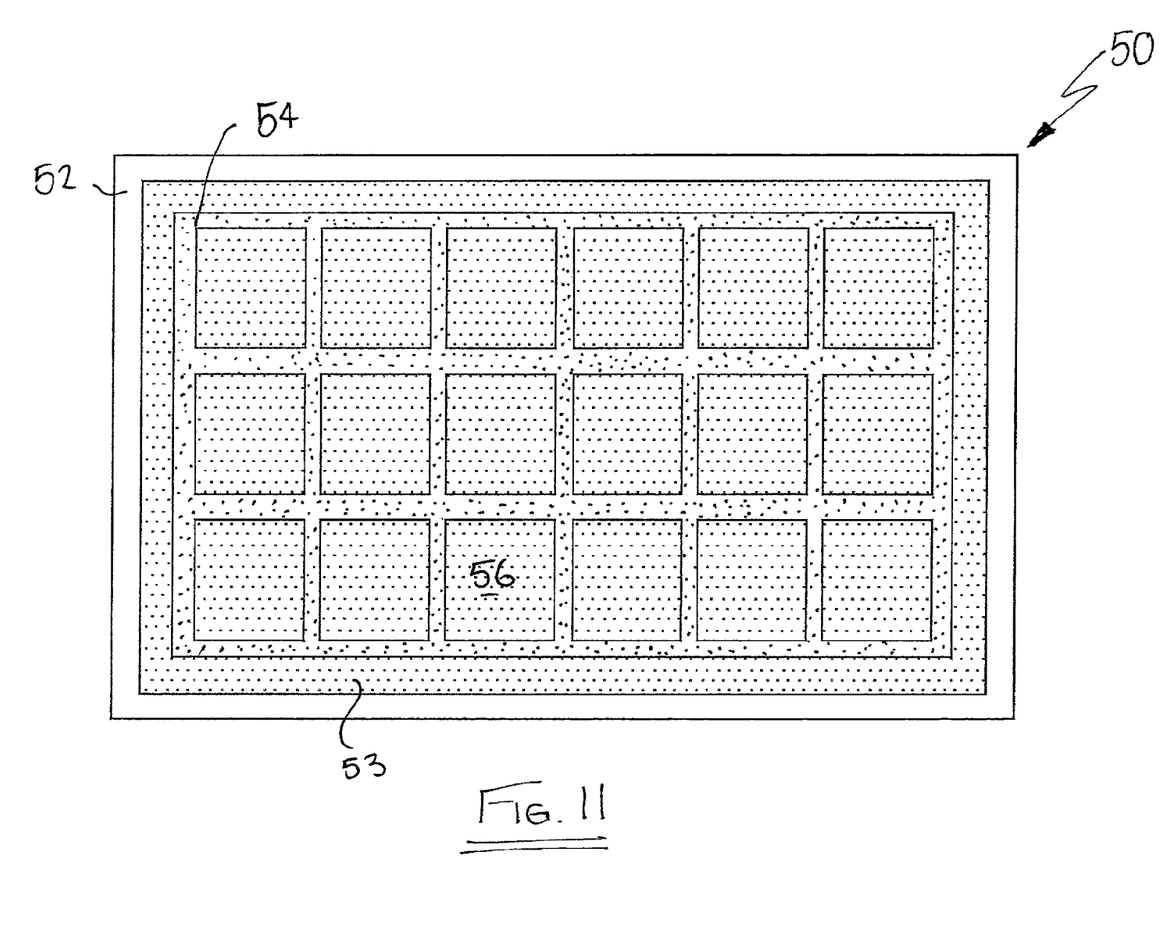
FIG. 11 is a plan view of the cold pack of the present invention with the outer and inner pouch combined.

FIGS. 9-11 depict an embodiment of a cold pack 50 to be used with the embodiments of the apparatus 10, 20, 30 and 40 discussed above. Whilst the pack 50 will be described below to refer to a single cold pack, it will be appreciated that for each apparatus 10, 20, 30 and 40, a specific cold pack 50 having dimensions specific for each apparatus will be provided.

The cold pack 50 comprises an inner pouch 54 and an outer pouch 52 which are combined together to form the cold pack 50. The cold pack 50 is shaped to fit the pouch provided in the central body portion of the apparatus 10, 20, 30 and 40.

The inner pouch 54 is depicted in FIG. 10 and comprises a pack of individual cells 55 filled with a phase change material 56 having a depressed freezing point. In one embodiment the phase change material 56 is a gel having a freezing point of around −10° C. However, it will be appreciated that the freezing point of the phase change material 56 may vary depending upon the application in which it is to be used. The phase change material or gel 56 may harden upon freezing and as such, the freezing point of the phase chance material may be selected to ensure that the material remains pliant and malleable, even at low temperatures. Each cell 55 is isolated from its neighbouring cell by way of a spaced region 57. The inner pouch 54 is preferably made from a nylon PE material, although the material may vary to include any variety of plastic or non-plastic materials having flexible properties.

The inner pouch 54 is configured to be inserted into the outer pouch 52, and the outer pouch 52 is able to be sealed to maintain the inner pouch 54 in position therein. The outer pouch 52 comprises a second phase change material 53 that may have a freezing point the same as, or different to, the phase change material 56 of the inner pouch 54. In one embodiment, the second phase change material 53 may have a freezing point that is even more depressed than the freezing point of the phase change material 56 of the inner pouch 54. In one embodiment the phase change material 53 is a gel having a freezing point of −18° C. The phase change material 53 is of a type that remains soft when frozen.

When the inner pouch 54 is inserted into the outer pouch 52, the second phase change material 53 flows around each of the cells 55 of the inner pouch 54 and into the spaced region 57 that is provided between the individual cells 55. In situations where the second phase change material 53 has a more depressed freezing point than the first phase change material 56, it remains soft when the first phase change material is hard. This arrangement offers flexibility and provides a cushioning effect around the first phase change material 56 when it is hard or frozen even though both materials are at substantially the same temperature. As a result, the multi-layered arrangement provides a cold pack 50 that is soft and has a degree of malleability of shape when inserted into the pouch of the apparatus 10, 20, 30 and 40.

In situations where the second phase change material 53 has a more depressed freezing point than the first phase change material 56, the combined cold pack 50 is maintained cold for a longer period of time. This, in combination with the increased surface area of the cold pack ensures that the cold pack remains colder for longer and is more comfortable to use than conventional ice application systems. In situations where the second phase change material 53 and the first phase change material 56 are of the same or similar freezing point, the combined system still functions to retain the cold pack colder for longer due to the interaction between the two materials.

Figure 12:
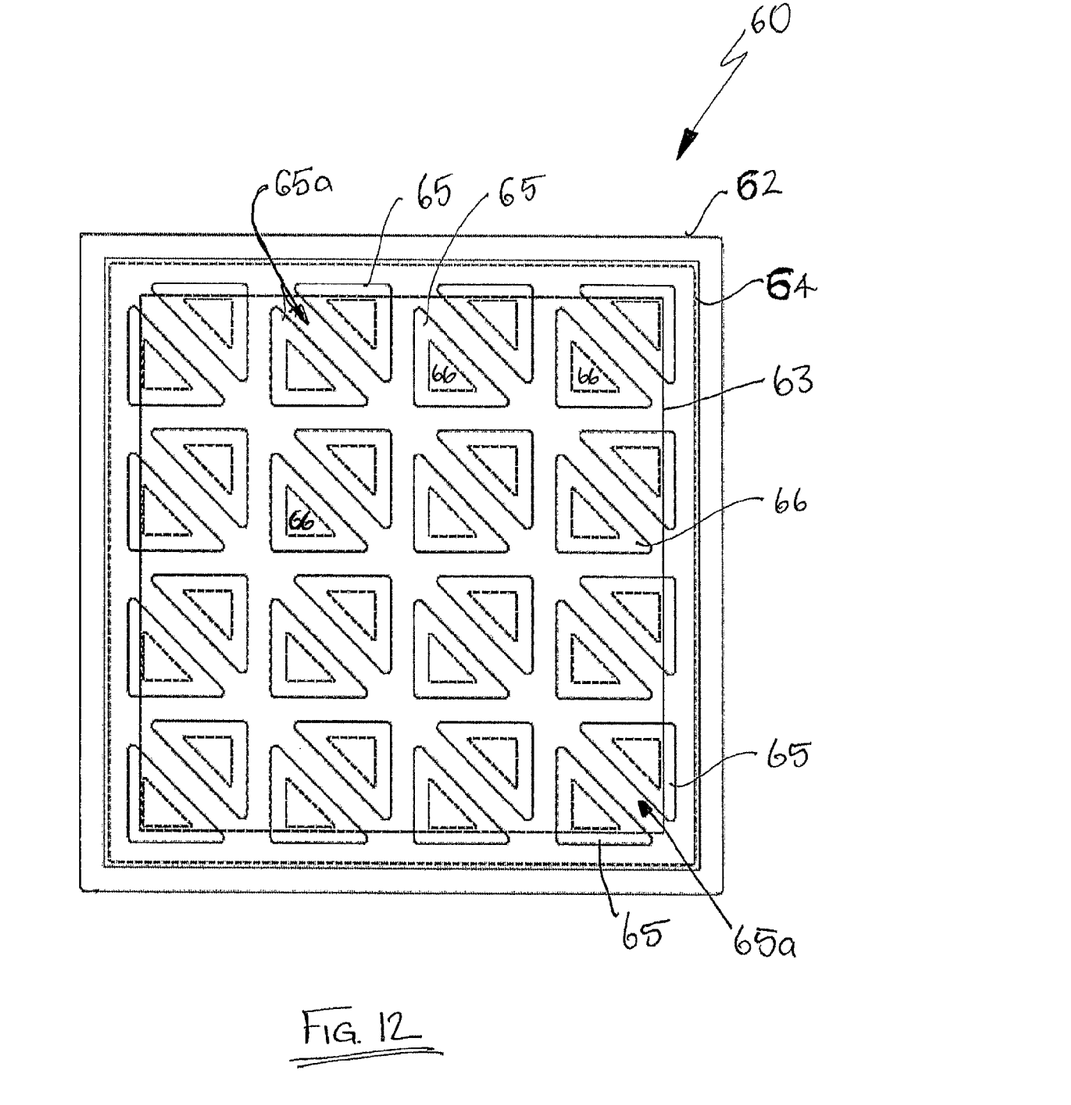
FIG. 12 is a plan view of a cold pack of the present invention with the in accordance with another embodiment.

Yet another embodiment of an icepack 60 for use with the present invention is depicted in FIG. 12. This embodiment is structured similarly to the icepack 50 with the exception being that the individual cells 65 have a triangular shape rather than a substantially square shape, and are separated by a gap 65a.

Each of the individual cells 65 are filled with a phase change material 66 having a depressed freezing point. In one embodiment the phase change material 66 is a gel having a −10° C.-18° C. freezing point. The gel 66 may harden upon freezing, with each cell 65 being isolated from its neighbouring cell by way of a gap 65a. Such a configuration ensures that the combined icepack remains flexible, even if the cells harden due to freezing of the phase change material due to the ability of the cells to move with respect to each other. The inner pouch 64 which contains the cells 65 is preferably made from a nylon PE material.

The inner pouch 64 is inserted into the outer pouch 62 and the outer pouch 62 is sealed to maintain the inner pouch 64 in position. The outer pouch 62 is preferably made from a combined PE and PA material and comprises an outer and an inner layer of second phase change material 63 having a freezing point that may be the same as, or more depressed than the freezing point of the phase change material 66 of the inner pouch 64. In one embodiment the phase change material 63 is a gel having a freezing point of −18° C. The phase change material 63 is of a type that remains soft when frozen and in the embodiment of FIG. 12, only one layer is shown, with the other layer being immediately behind the inner pouch 64.

As previously discussed, in the embodiment of the cold pack of FIG. 12, when the inner pouch 64 is inserted into the outer pouch 62, the second phase change material 63 flows around each of the cells 65 of the inner pouch 64 and into the spaced region 67 and gap 65a that is provided between the individual triangular cells 65. As the second phase change material 63 has the same or more depressed freezing point than the first phase change material 66 and remains soft when at a low temperature, it offers flexibility and provides a cushioning effect around the harder first phase change material 66. This multi-layered arrangement provides a cold pack 60 that is soft and has a degree of malleability of shape when inserted into the pouch of the apparatus 10, 20, 30 and 40. As the cells 65 are made from a smaller and triangular shape, the individual cells 65 are able to move around in a freer manner which makes the icepack more malleable for use.

It will be appreciated that the combination of the apparatus which is capable of applying compression therapy as well as the cold pack that facilitates improved freezing times, the apparatus of the present invention provides a heat treatment device that is a considerable improvement over other systems available in the marketplace. For heat treatment applications, clay beads may be employed instead of the individual cells 65 filled with phase change material and rather than freezing the apparatus prior to use, the apparatus may be heated.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

It will be appreciated by those skilled in the art that many modifications and variations may be made to the methods of the invention described herein without departing from the spirit and scope of the invention.

The claims defining the invention are as follows:

1. A temperature treatment apparatus, comprising:
    a body made from a flexible and expandable material for attachment to a predetermined region of the human body requiring treatment, the body having a space formed within the flexible and expandable material; and
    a temperature radiating element located within the space formed within the flexible and expandable material of the body, the temperature radiating element being configured to have a soft and malleable shape profile to apply temperature treatment to the predetermined region of the human body;
    wherein the temperature radiating element comprises an inner pouch containing a first phase change material that is insertable within an outer pouch comprising a second phase change material, such that, upon insertion, the inner pouch is substantially encapsulated within the second phase change material of the outer pouch and when the body is attached to the predetermined region of the human body requiring treatment, the flexible and expandable material compresses the temperature radiating element against the predetermined region of the human body requiring treatment, so that said temperature treatment apparatus providing both temperature treatment and compression treatment to the predetermined region of the human body requiring treatment.

2. The temperature treatment apparatus according to claim 1, wherein the inner pouch and the outer pouch of the temperature radiating element are freezable for applying cold therapy to the predetermined region of the human body.

3. The temperature treatment apparatus according to claim 2, wherein the inner pouch is configured to comprising a plurality of individual pockets containing said first phase change material.

4. The temperature treatment apparatus according to claim 3, wherein the plurality of individual pockets are movable relative to each adjacent pocket.

5. The temperature treatment apparatus according to claim 3, wherein when the inner pouch is insertable within the outer pouch comprising a second phase change material, the second phase change material being configured to flow over and between the plurality of individual pockets so as to substantially encapsulate the individual pockets within the second phase change.

6. The temperature treatment apparatus according to claim 1, wherein the first phase change material has a freezing point that is substantially the same as the second phase change material.

7. The temperature treatment apparatus according to claim 6, wherein the second phase material is a soft material when frozen and forms a soft layer about the first phase material.

8. The temperature treatment apparatus according to claim 1, wherein the body comprises one or more arm members configured to extend around said human body, said arm members being secured with respect to said human body for causing the flexible and expandable material of the body to expand, so that the body applies a compression force to the predetermined region of the human body.

9. The termperature treatment apparatus according to claim 1, wherein the first phase change material has a freezing point that is higher than the freezing point of the second phase change material.

\* \* \* \* \*